United States Patent
Chau et al.

(10) Patent No.: US 9,612,197 B2
(45) Date of Patent: Apr. 4, 2017

(54) REFLECTION-BASED TUBULAR WAVEGUIDE PARTICLE PLASMON RESONANCE SENSING SYSTEM AND SENSING DEVICE THEREOF

(71) Applicant: National Chung Cheng University, Chia-Yi (TW)

(72) Inventors: Lai-Kwan Chau, Chiayi (TW); Yu-Chung Huang, Taichung (TW); Chih-To Wang, Kaohsiung (TW); Chien-Hsing Chen, New Taipei (TW); Chang-Yue Chiang, Taichung (TW)

(73) Assignee: National Chung Cheng University, Chia-Yi (TW)

( * ) Notice: Subject to any disclaimer, the term of this patent is extended or adjusted under 35 U.S.C. 154(b) by 13 days.

(21) Appl. No.: 14/806,321

(22) Filed: Jul. 22, 2015

(65) Prior Publication Data

US 2016/0216205 A1 Jul. 28, 2016

(30) Foreign Application Priority Data

Jan. 23, 2015 (TW) .............................. 104102284 A

(51) Int. Cl.
*G01N 21/552* (2014.01)
(52) U.S. Cl.
CPC ....... *G01N 21/554* (2013.01); *G01N 2201/08* (2013.01)
(58) Field of Classification Search
CPC ............. G01N 21/554; G01N 2201/08; G01N 2201/068

(Continued)

(56) References Cited

U.S. PATENT DOCUMENTS 8,072,606 B2* 12/2011 Chau .................... G01N 21/554
356/445
8,216,518 B2* 7/2012 Chau .................... G01N 21/554
356/445

(Continued)

FOREIGN PATENT DOCUMENTS

| TW | I383139 B1 | 1/2013 |
|----|------------|--------|
| TW | I399532 B1 | 6/2013 |
| TW | I457626 B  | 10/2014 |

OTHER PUBLICATIONS

Office Action of corresponding TW application, published on Jan. 6, 2016.

*Primary Examiner* — Sang Nguyen
(74) *Attorney, Agent, or Firm* — Wang Law Firm, Inc.

(57) ABSTRACT

A reflection-based tubular waveguide particle plasmon resonance sensing system and a sensing device thereof are provided. The sensing device includes a hollow tubular waveguide element having wall, a reflection layer disposed on one end of the wall (distal end), and a noble metal nanoparticle layer distributed on the surface of the wall. An incident light enters the wall through another end of the tubular waveguide element (proximal end) and being total internal reflected many times along the wall, then is reflected by the reflection layer and being total internal reflected many times along the wall again, and finally, the incident light exits the proximal end. Wherein, when the sample contacts the noble metal nanoparticle layer of the tubular waveguide element, the particle plasmon resonance condition is altered and hence the signal intensity of the light exiting the tubular waveguide element changes.

13 Claims, 7 Drawing Sheets

(58) Field of Classification Search
USPC ..................................... 356/455, 246, 244
See application file for complete search history.

(56) References Cited

U.S. PATENT DOCUMENTS

| | | | |
|---|---|---|---|
| 8,355,134 B2 * | 1/2013 | Chau ..................... | B82Y 20/00 356/445 |
| 2010/0123900 A1 * | 5/2010 | Chau .................... | G01N 21/554 356/445 |
| 2010/0171958 A1 * | 7/2010 | Chau .................... | G01N 21/554 356/445 |
| 2010/0182607 A1 * | 7/2010 | Chau .................... | G01N 21/554 356/445 |
| 2011/0090506 A1 * | 4/2011 | Chau .................... | G01N 21/554 356/445 |
| 2014/0028995 A1 * | 1/2014 | Bratkovski ............ | G01N 21/01 356/38 |
| 2015/0080666 A1 * | 3/2015 | Vayser ................. | A61M 1/008 600/245 |

\* cited by examiner

REFLECTION-BASED TUBULAR WAVEGUIDE PARTICLE PLASMON RESONANCE SENSING SYSTEM AND SENSING DEVICE THEREOF

CROSS-REFERENCE TO RELATED APPLICATION

This application claims priority from Taiwan Patent Application No. 104102284, filed on Jan. 23, 2015, in the Taiwan Intellectual Property Office, the content of which are hereby incorporated by reference in their entirety for all purposes.

BACKGROUND OF THE INVENTION

1. Field of the Invention

This application relates to a plasmon resonance sensing system and a sensing device thereof, and more particularly, to a reflection-based tubular waveguide particle plasmon resonance sensing system and a sensing device thereof.

2. Description of the Related Art

Most conventional biological sensing methods require the use of sophisticated and expensive instruments in medical institutions or specialized laboratories, or need to be labeled before performing the detection. The steps are lengthy, complicated and time-consuming. In recent years, the biochemical sensing platform is directed towards low cost, miniaturization, real-time detection, and so on, making the label-free bio-sensing techniques to get the attention. As an example, many label-free biosensors using the technique of surface plasmon resonance have been developed nowadays. With advances in the nanotechnology, the particle plasmon resonance (PPR) sensing technology has been widely studied and used in the development of the label-free bio-sensing technology.

The current particle plasmon resonance sensing technique generates the particle plasmon resonance by either the transmission mode with a single pass of light or reflection mode with a double pass of light through a submonolayer of noble metal nanoparticles on a substrate. However, the absorbance is low by such methods, resulting in insufficient performance. Furthermore, such methods typically require a high-resolution spectrophotometer and hence the objectives of low cost, miniaturization, real-time detection are not achieved.

SUMMARY OF THE INVENTION

In view of the foregoing technical problems, the objective of the present invention provides a reflection-based tubular waveguide particle plasmon resonance sensing system and a sensing device thereof, which use the waveguide material combining with multiple total internal reflections and the evanescent wave to generate the particle plasmon resonance. Hereby, a probe-type biosensing platform having low cost, miniaturization, label-free, high-sensitivity, real-time detection is developed.

In order to achieve the aforementioned objective, the present invention provides reflection-based tubular waveguide particle plasmon resonance sensing device which may include a hollow tubular waveguide element having a wall, wherein two openings are disposed at a distal end and a proximal end opposed to each other of the hollow tubular waveguide element; a reflection layer disposed on the distal end of the wall of the hollow tubular waveguide element, wherein a light enters the wall through the proximal end and is total internal reflected many times along the wall, then the light is reflected by the reflection layer and is total internal reflected many times along the wall again, then the light exits the wall through the proximal end; and a noble metal nanoparticle layer having a plurality of noble metal nanoparticles is distributed on a surface of the wall, wherein when a sample contacts the noble metal nanoparticle layer, the particle plasmon resonance condition is altered by the sample, and hence the signal intensity of the light exiting the proximal end of the hollow tubular waveguide element changes.

Preferably, the material of the hollow tubular waveguide element may be a transparent material.

Preferably, the noble metal nanoparticle layer may have a plurality of noble metal nanoballs, a plurality of noble metal nanorods, a plurality of noble metal nanoshells, a plurality of noble metal nanorings, a plurality of noble metal nanoplates, a plurality of noble metal nano dendrimer-like, a plurality of noble metal nanocubes, a plurality of noble metal nanoprisms, a plurality of noble metal nanonetworks, or the combination thereof.

Preferably, the noble metal nanoparticle layer may be modified by a recognition unit, such as chemical recognition molecule, antibody, antigen, lectin, hormone receptor, nucleic acid, carbohydrate, or so on, for being applied to detecting different substances, wherein when the sample contacts the noble metal nanoparticle layer and an analyte in the sample binds with the recognition unit, the particle plasmon resonance condition may be altered and hence the signal intensity of the light exiting the proximal end of the hollow tubular waveguide element changes.

Preferably, the material of the distal end of the hollow tubular waveguide element may be a reflective material for being used as the reflection layer.

Preferably, the reflection-based tubular waveguide particle plasmon resonance sensing device may further include a refractive index adjustment layer disposed on another surface of the wall without the noble metal nanoparticle layer or further on part of the surface with the noble metal nanoparticle layer for avoiding the light being disturbed by the sample outside the wall when the sample contacts the another surface of the wall without the noble metal nanoparticle layer, wherein the refractive index of the refractive index adjustment layer is lower than the refractive index of the hollow tubular waveguide element.

In addition, the present invention further provides a reflection-based tubular waveguide particle plasmon resonance sensing system which may include at least one light emitting device for providing at least one light; a hollow tubular waveguide element having a wall, wherein two openings are disposed at a distal end and a proximal end opposed to each other of the hollow tubular waveguide element, wherein the light enters the wall through the proximal end and is total internal reflected many times along the wall; a reflection layer disposed on the distal end of the wall of the hollow tubular waveguide element and reflecting the light entered in the wall, such that the light is total internal reflected many times along the wall again and exits the wall through the proximal end; a noble metal nanoparticle layer having a plurality of noble metal nanoparticles is distributed on a surface of the wall, wherein when a sample contacts the noble metal nanoparticle layer, the particle plasmon resonance condition is altered by the sample, and hence the signal intensity of the light exiting the proximal end of the hollow tubular waveguide element changes; and at least one photodetector disposed on the side of the proximal end of the hollow tubular waveguide element, wherein the photodetector detects the light exited the wall through the proximal end for determining the sample.

Preferably, the reflection-based tubular waveguide particle plasmon resonance sensing system may further include a refractive index adjustment layer disposed on another surface of the wall without the noble metal nanoparticle layer or further on part of the surface with the noble metal nanoparticle layer for avoiding the light being disturbed by the sample outside the wall when the sample contacts the another surface of the wall without the noble metal nanoparticle layer, wherein the refractive index of the refractive index adjustment layer is lower than the refractive index of the hollow tubular waveguide element.

Preferably, the noble metal nanoparticle layer may be modified by a recognition unit for being applied to detecting an analyte in a sample, wherein when the sample contacts the noble metal nanoparticle layer and an analyte in the sample binds with the recognition unit, the particle plasmon resonance condition is altered and hence the signal intensity of the light exiting the proximal end of the hollow tubular waveguide element changes.

Preferably, the reflection-based tubular waveguide particle plasmon resonance sensing system may further include a moving device holding the light emitting device, the hollow tubular waveguide element, the reflection layer, the noble metal nanoparticle layer, and the photodetector, wherein the moving device is configured to move the light emitting device, the hollow tubular waveguide element, the reflection layer, the noble metal nanoparticle layer, and the photodetector. Wherein, when the reflection-based tubular waveguide particle plasmon resonance sensing system of the present invention further include the refractive index adjustment layer, the moving device further holds the refractive index adjustment layer for moving the position of the refractive index adjustment layer relative to the sample.

Preferably, the reflection-based tubular waveguide particle plasmon resonance sensing system may further include at least one sample container holding the sample and being disposed on one side of the hollow tubular waveguide element.

Preferably, the reflection-based tubular waveguide particle plasmon resonance sensing system may further include a suction device disposed on one side of the hollow tubular waveguide element for drawing a sample into the hollow tubular waveguide element.

Preferably, the material of the hollow tubular waveguide element may be a transparent material.

Therefore, a reflection-based tubular waveguide particle plasmon resonance sensing system and a sensing device thereof disclosed in the present invention may have one or more advantages as follows.

1. Because of the good mechanical strength of the tubular waveguide element, there is no need to make a chip to hold the tubular waveguide element. As a result, the manufacturing time and cost of the reflection-based tubular waveguide particle plasmon resonance sensing system and a sensing device thereof can be reduced.

2. By means of a hollow tubular waveguide element having a wall, wherein two openings are disposed at a distal end and a proximal end opposed to each other of the hollow tubular waveguide element, a miniaturized biosensing platform is easily achieved.

3. By combining the hollow tubular waveguide element, which has openings disposed at a distal end and a proximal end and is merely used as the sensing element, with the other system element on a three-axis platform, the stability of the platform is increased. By moving the axis Z of the three-axis platform to place the hollow tubular waveguide element in a liquid sample to perform the detection, the problem of air-bubbles can be avoided and also the alignment error can be reduced.

4. Applying the hollow tubular waveguide element having openings disposed at a distal end and a proximal end as the sensing element, both the internal and external walls become the sensing region. Hence, the present invention has a larger sensing region when immersed in a sample at the same depth.

5. The reflection layer applied in the present invention enables the sensing system disclosed in the present invention becoming a reflection-based sensing platform (reflection-based means that the light source and the detector are at different locations but on the same side), so that the incident light is transmitted through the optical path twice to enhance the effect of the particle plasmon resonance. Hereby, the sensor sensitivity is increased.

6. Applying the hollow tubular waveguide element having openings disposed at a distal end and a proximal end as a probe to perform the detection, the sensing platform is able to be used in various detection applications (e.g. diagnostics of animal and plants diseases, environmental monitoring, food analysis, clinical diagnostics, and so on) according to the user's requirements (e.g. the sample container can be ELISA 96 well plate, centrifuge tube, sample bottle, or so on), so as to promote the convenience.

DETAILED DESCRIPTION OF THE PREFERRED EMBODIMENTS

Hereinafter, embodiments of the present invention will be described in detail with reference to the accompanying drawings so that those skilled in the art to which the present invention pertains can realize the present invention. As those skilled in the art would realize, the described embodiments may be modified in various different ways, all without departing from the spirit or scope of the present invention.

Figure 1:
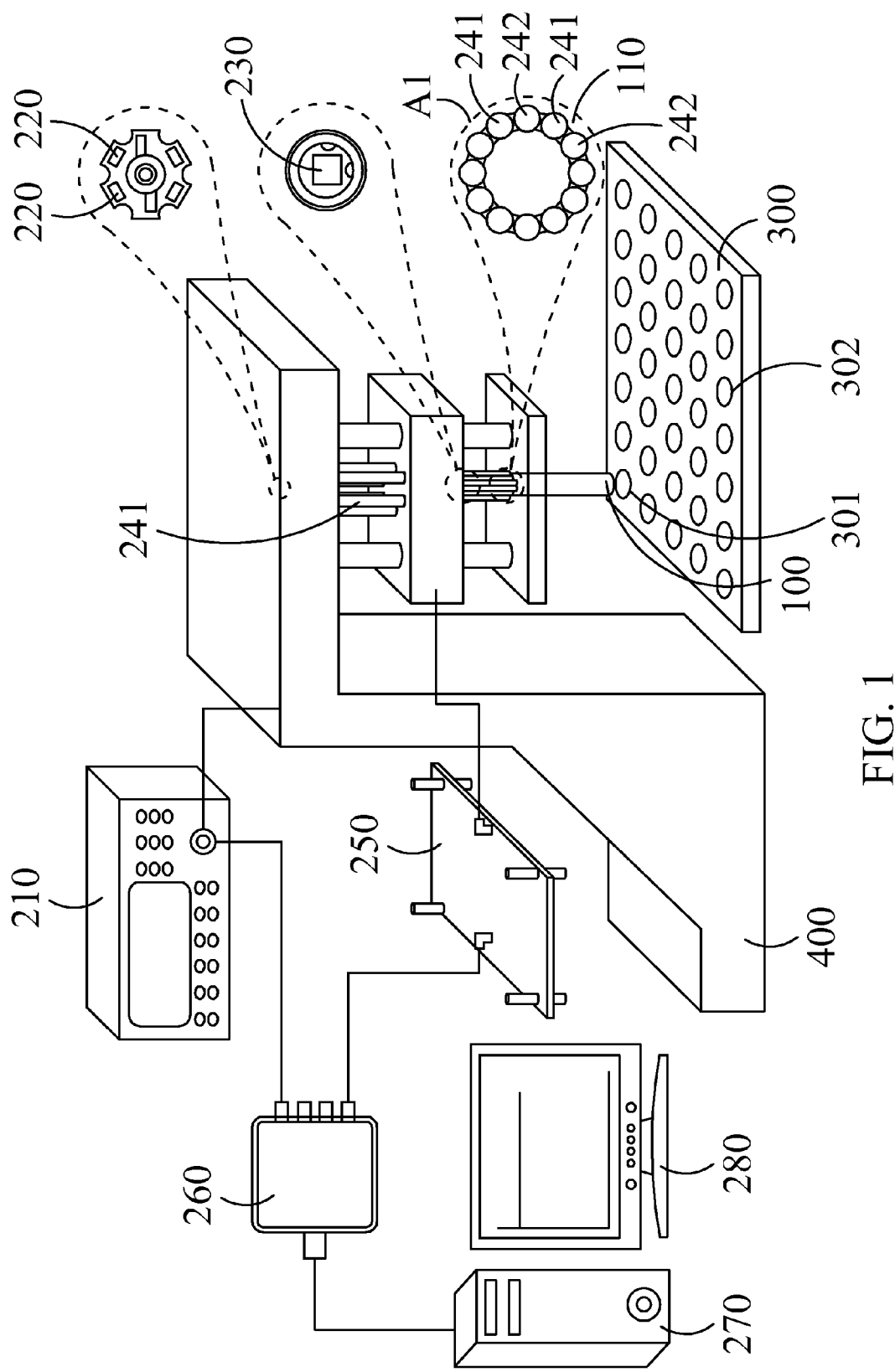
FIG. 1 is a schematic diagram of a reflection-based tubular waveguide particle plasmon resonance sensing device of the present invention.
Figure 2:
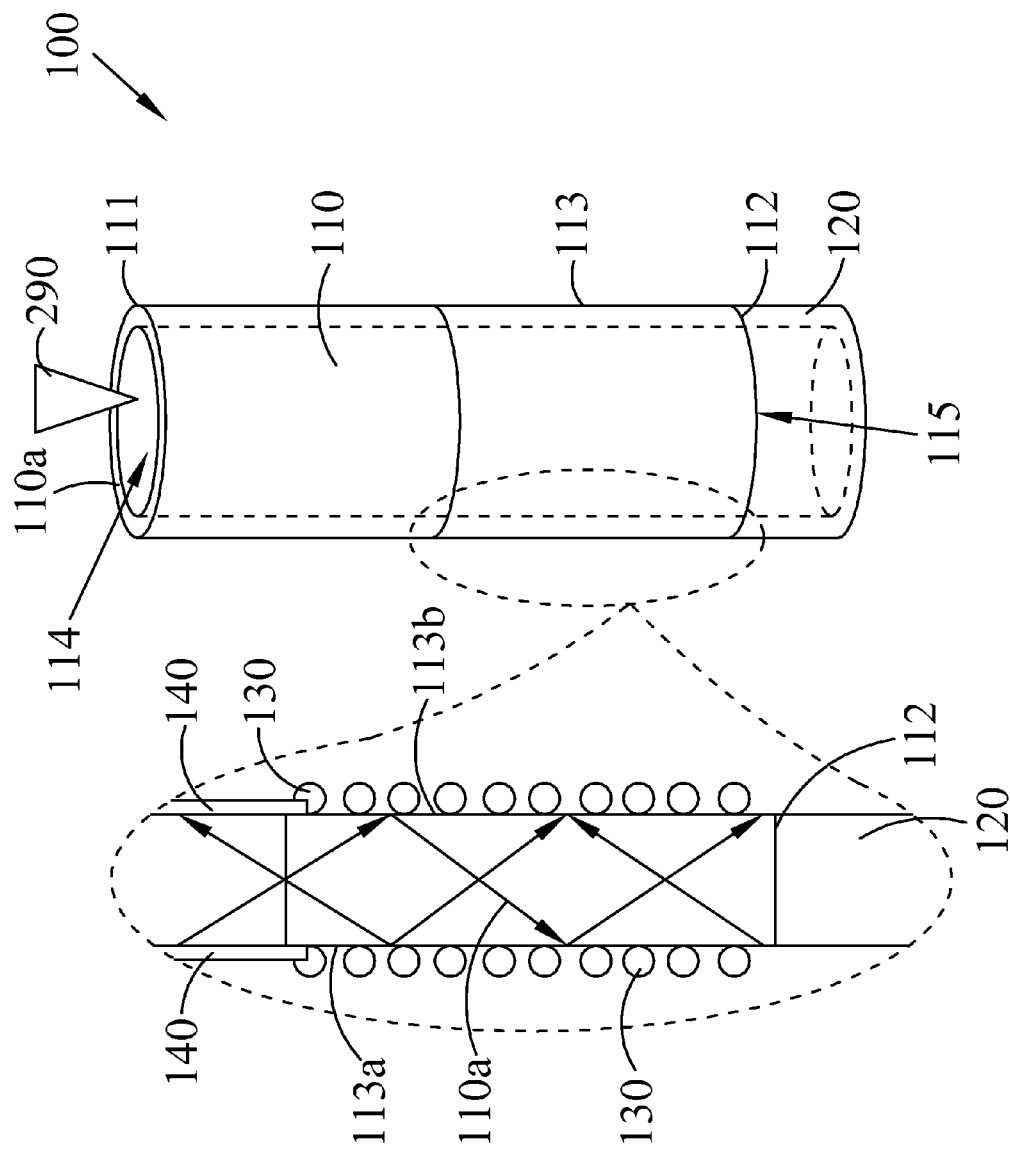
FIG. 2 is a structural schematic diagram of a reflection-based tubular waveguide particle plasmon resonance sensing device of the present invention.
Figure 3:
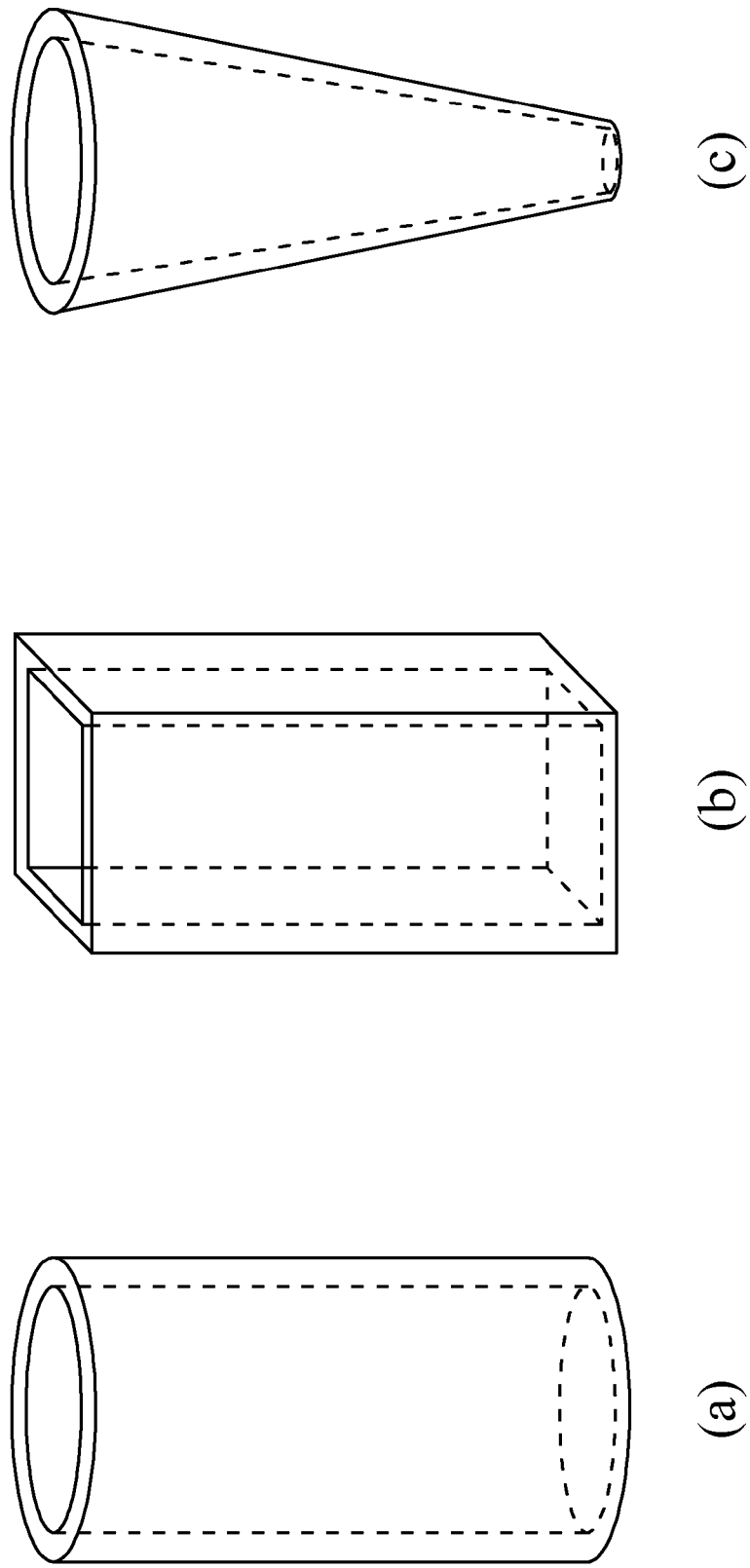
FIG. 3 is a schematic diagram showing a reflection-based tubular waveguide particle plasmon resonance sensing device of the present invention made of different types of hollow tubular waveguide configurations.

Please refer to FIG. 1 to FIG. 3 which are schematic diagrams of a reflection-based tubular waveguide particle plasmon resonance sensing device of the present invention, a structural schematic diagram of a reflection-based tubular waveguide particle plasmon resonance sensing device of the present invention, and a schematic diagram showing a reflection-based tubular waveguide particle plasmon resonance sensing device of the present invention made of different types of hollow tubular waveguide configurations, respectively.

As shown in FIG. 1 to FIG. 3, a reflection-based tubular waveguide particle plasmon resonance sensing system of the present invention comprises at least one light emitting device 220, a reflection-based tubular waveguide particle plasmon resonance sensing device 100 and a photodetector 230. Wherein, the reflection-based tubular waveguide particle plasmon resonance sensing device 100 comprises a hollow tubular waveguide element 110, a reflection layer 120 and a noble metal nanoparticle layer 130. The hollow tubular waveguide element 110 has a wall 110a, wherein two openings 114, 115 are disposed at a distal end 112 and a proximal end 111 opposed to each other of the hollow tubular waveguide element 110, such that the hollow tubular waveguide element 110 may become a tubular waveguide element having two openings disposed at the distal end 112 and the proximal end 111 opposed to each other. Wherein, the hollow tubular waveguide element 110 may be made of a light transmissible material, so that the hollow tubular waveguide element 110 becomes transparent or translucent. For example, the hollow tubular waveguide element 110 may be made of glass, transparent polymers or other materials which light can be transmitted. The mechanical strength of the hollow tubular waveguide element 110 may be better than the known optical fiber. The hollow tubular waveguide element 110 may have about 30 mm in length, 5 mm in outer diameter, and 0.8 mm in thickness of the wall 110a, but it shall be not limited thereto. In addition, the hollow tubular waveguide element 110 may have shaped as a cylinder (as shown in (a) of FIG. 3), rectangular cylinder (as shown in (b) of FIG. 3) or a hopper having a wider upper and a narrower bottom (as shown in (C) of FIG. 3), but the present invention shall be not limited thereto. For example, the hollow tubular waveguide element 110 may be a polygonal cylinder or a cone having a narrower upper and a wider bottom.

The noble metal nanoparticle layer 130 is distributed on at least one surface of the wall 110a of the hollow tubular waveguide element 110, and has a plurality of noble metal nanoparticles. When a sample contacts the hollow tubular waveguide element 110 and an analyte in the sample binds with the recognition unit, the particle plasmon resonance (PPR) condition of the metal nanoparticle layer 130 is altered and hence the signal intensity of the light exiting the proximal end 111 of the hollow tubular waveguide element changes.

Wherein the noble metal nanoparticle may be such as noble metal nanoballs, noble metal nanorod, noble metal nanoshell, noble metal nanoring, noble metal nanoplate, noble metal nano dendrimer-like, noble metal nanocube, noble metal nanoprism, noble metal nanonetwork, the other appropriate noble metal nanoparticles, or the combination thereof. Besides, the material of the noble metal nanoparticle may be gold, silver, copper, graphene or other appropriate noble metals.

For example, the hollow tubular waveguide element 110 has a sensing region 113, wherein the sensing region 113 is close to or adjacent to the distal end 112. The wall 110a within the sensing region 113 has an external side surface 113a facing outward and an internal side surface 113b facing inward, and the noble metal nanoparticle layer 130 is coated or formed on the external side surface 113a and the internal side surface 113b, such that the sample contacts both of the noble metal nanoparticle layer 130 on the external side surface 113a and the noble metal nanoparticle layer 130 on the internal side surface 113b to enhance the variation of the signal intensity of the light within the wall 110a. Wherein, the sensing region 113 of the hollow tubular waveguide element 110 can be cleaned to remove the impurity before being used, and then the noble metal nanoparticle layer 130 is formed on both of the external side surface 113a and the internal side surface 113b. In addition, the noble metal nanoparticle layer 130 can further be modified by a recognition unit (not shown), such as chemical recognition molecule, antibody, antigen, lectin, hormone receptor, nucleic acid, or sugar, and so on, for being applied to detecting different substances. Wherein, each of the recognition units can bind specifically with one analyte to increase the specificity of the detection and to cause the variation of the signal intensity of the light within the wall 110a.

In addition, the reflection layer 120 is disposed at the distal end 112 of the wall 110a of the hollow tubular waveguide element 110. When the incident light enters the wall 110 through the proximal end 111 and is total internal reflected many times along the wall, the incident light produces the evanescent wave on both of the external side surface 113a and the internal side surface 113b within the sensing region 113 for generation of the particle plasmon resonance. Afterwards, when the incident light passes through the wall 110a from the proximal end 111 and reaches the reflection layer 120 disposed on the distal end 112, the incident light is reflected by the reflection layer 120 and moves towards the proximal end 111. Wherein, during the propagation of the incident light towards the proximal end 111 after reflection by the reflection layer 120, the incident light is total internal reflected many times along the walls again, so that the incident light produces the evanescent wave on both of the external side surface 113a and the internal side surface 113b within the sensing region 113 again. Hereby, the variation of the light intensity within the wall 110a is increased further. Then, the incident light within the wall 110a exits the wall 110a through the proximal end 111. Wherein, the material of the distal end 112 of the hollow tubular waveguide element 110 may be a reflective material for being served as the reflection layer 120. Under such situation, the sensing region 113 is near the distal end 112 and adjacent to the reflection layer 120. Besides, the reflection layer 120 of the present invention can be disposed at the distal end 112 of the hollow tubular waveguide element 110 and adjacent to the sensing region 113.

Thus, the reflection-based tubular waveguide particle plasmon resonance sensing device 100 of the present invention may have a better mechanical strength based on the hollow tubular waveguide element 110, such that the need of making a chip to hold the tubular waveguide element is not necessary, and the manufacturing time and the cost can thereby be reduced. Besides, the reflection-based tubular waveguide particle plasmon resonance sensing device 100 of the present invention may be developed as a miniaturized biosensing platform by employing the hollow tubular waveguide element 110, which has two openings at the opposite two ends, as the sensing element. Besides, because both the external side surface 113a and the internal side surface 113b of the wall 110a of the hollow tubular waveguide element 110 can contact the sample at the same time, the reflection-based tubular waveguide particle plasmon resonance sensing device 100 of the present invention may have a larger sensing area when immersed in a sample at the same depth. Moreover, based on the reflection layer 120, the sensing system of the present invention becomes a reflection-based sensing platform (reflection-based means that the light source and the detector are at different locations but on the same side), so that the incident light is transmitted through the optical path twice to enhance the effect of the particle plasmon resonance. Hereby, the sensor sensitivity is increased.

Furthermore, the reflection-based tubular waveguide particle plasmon resonance sensing system and the sensing device thereof of the present invention can further comprise a refractive index adjustment layer 140. The refractive index adjustment layer 140 is disposed on some parts of the surface of the wall 110a of the hollow tubular waveguide element 110, say, on another surface of the wall without the noble metal nanoparticle layer 130. Thus, when the light enters into the part of the wall 110a without the noble metal nanoparticle layer 130 and the sample contacts the another surface of the wall 110a without the noble metal nanoparticle layer 130, the condition of the total internal reflection of light within the wall 110a being disturbed by the sample outside the wall 110a can be avoided. Wherein, the refractive index of the refractive index adjustment layer 140 is lower than that of the hollow tubular waveguide element 110 for avoiding the above interference. However, it should be emphasized that the refractive index adjustment layer 140 shall be not limited to merely disposing on the surface without the noble metal nanoparticle layer 130 when the reflection-based tubular waveguide particle plasmon resonance sensing system and the sensing device thereof of the present invention has the refractive index adjustment layer 140. In other words, the refractive index adjustment layer 140 may be not only disposed on the surface without the noble metal nanoparticle layer 130, but also further disposed on a partial portion of the surface with the noble metal nanoparticle layer 130, such as further disposed on some part of the internal side surface 113a and/or the external side surface 113b, according to the actual process or other reasons.

In addition, at least one light emitting device 220 provides at least one light. The at least one light enters the wall 110a through the proximal end 111 and is total internal reflected many times along the wall 110a. After the light is reflected back to the sensing region 113 by the reflection layer 120 located at the distal end 112 and is total internal reflected many times along the wall 110a again, the light exits the wall 110a via the proximal end 111 and becomes the emergent light. At least one photodetector 130 is disposed on the side of the proximal end 111 of the hollow tubular waveguide element 110, wherein the photodetector 230 detects the emergent light exited the wall 110a through the proximal end 111 for determining the characteristics, such as refractive index, concentration, and so on, of the sample.

For example, the reflection-based tubular waveguide particle plasmon resonance sensing system of present invention can further comprises a sample container 301 to hold the sample. The sample container 301 is disposed on one side near or at the distal end 112 of the hollow tubular waveguide element 110. Thus, when the reflection-based tubular waveguide particle plasmon resonance sensing device 100 in the form of a probe is placed in the sample container 301, the sample in the sample container 301 may enter into the hollow tubular waveguide element 110 and contact with the noble metal nanoparticle layer 130 disposed on the internal side wall 113b. In addition, the sample in the sample container 301 may also contact the noble metal nanoparticle layer 130 disposed on the external side wall 113a, such that the present invention has a larger sensing area when immersed in the sample at the same depth. Besides, the reflection-based tubular waveguide particle plasmon resonance sensing system of the present invention can further comprise a suction device 290 disposed at the side near the proximal end 111 of the hollow tubular waveguide element 110 for drawing the sample into the hollow tubular waveguide element 110, such that the volume drawing into the hollow tubular waveguide element 110 is clearly defined and the time of the sample passing through the hollow tubular waveguide element 110 may be decreased. Wherein, the sample container 301 may be ELISA 96 well plate, centrifuge tube, sample bottle, or other kinds of containers which meet the user's requirements.

In addition, the reflection-based tubular waveguide particle plasmon resonance sensing system of the present invention can further comprise a sample container plate 300 disposed at the side near the distal end 112 of the hollow tubular waveguide element 110. The sample container plate 300 has a plurality of sample containers 301, 302 to accommodate a number of samples, such that the reflection-based tubular waveguide particle plasmon resonance sensing device 100 can be placed into the sample containers 301, 302 sequentially, or a multiple of reflection-based tubular waveguide particle plasmon resonance sensing devices 100 can be employed for simultaneous detection in order to increase the throughput of the analysis. For example, the reflection-based tubular waveguide particle plasmon resonance sensing system of the present invention can further comprise a moving device 400 holding the light emitting device 220, the reflection-based tubular waveguide particle plasmon resonance sensing device 100, and the photodetector 230, wherein the reflection-based tubular waveguide particle plasmon resonance sensing device 100 at least comprises the hollow tubular waveguide element 110, the reflection layer 120, and the noble metal nanoparticle layer 130. The moving device 400 is configured to move the light emitting device 220, the photodetector 230, and the reflection-based tubular waveguide particle plasmon resonance sensing device 100 having the hollow tubular waveguide element 110, the reflection layer 120, and the noble metal nanoparticle layer 130. Consequently, the reflection-based tubular waveguide particle plasmon resonance sensing device 100 can be placed into the sample containers 301, 302, and so on, sequentially. Wherein, the light emitting device 220, the photodetector 230 and the reflection-based tubular waveguide particle plasmon resonance sensing device 100 may be respectively embedded, adhered or disposed at different positions of the moving device 400. Besides, the moving device 400 may be a three-axis moving platform, so that the moving device 400 is able to move the light emitting device 220, the photodetector 230 and the reflection-based tubular waveguide particle plasmon resonance sensing device 100 along the three axis respectively. When the reflection-based tubular waveguide particle plasmon resonance sensing device 100 further has the aforementioned refractive index adjustment layer 140, the moving device 400 is provided to accommodate the light emitting device 220, the photodetector 230, and the reflection-based tubular waveguide particle plasmon resonance sensing device 100 having the hollow tubular waveguide element 110, the reflection layer 120, the noble metal nanoparticle layer 130, and the refractive index adjustment layer 140 to move the position thereof.

Hence, the reflection-based tubular waveguide particle plasmon resonance sensing system of the present invention is able to perform the detection with the hollow tubular waveguide element 110 having two openings at the opposite sides by way of the probe-form, such that the sample containers 301, 302, and so on can be used to perform the various detection applications (e.g. diagnostics of animal and plant diseases, environmental monitoring, food analysis, and clinical diagnostics, etc.) according to the user's requirements, such as ELISA 96 well plate, centrifuge tube, sample bottle, and other kinds of containers, to promote the usage convenience. Moreover, by combining the hollow tubular waveguide element 110, which has openings disposed at a distal end 112 and a proximal end 111 and is only used as the sensing element, with the other element on the three-axis platform, the stability of the platform is increased. By moving the axis Z of the three-axis platform to place the hollow tubular waveguide element in a liquid sample to perform the detection, the problem of air-bubbles can be avoided and the alignment error can be effectively reduced.

In addition, the reflection-based tubular waveguide particle plasmon resonance sensing system of the present invention can further comprise a function generator 210 electrically connected to the light emitting device 220 to control the parameters (e.g. wavelength, light intensity, and/or so on) of the light emitted by the light emitting device 220. For example, the function generator 210 controls the light emitting device 220 to emit the green light having the wavelength of about 530 nm for being served as the incident light entering the wall 110a, but it shall be not limited thereto. Besides, the reflection-based tubular waveguide particle plasmon resonance sensing system of the present invention can further comprise a first optical fiber 241 disposed between the light emitting device 220 and the hollow tubular waveguide element 110. For example, one end point of the first optical fiber 241 is connected to the proximal end 111 of the wall 110a of the hollow tubular waveguide element 110, and the other end point is connected to the light emitting device 220, such that the light emitted by the light emitting device 220 can enter the wall 110a of the hollow tubular waveguide element 110 through the first optical fiber 241 for being served as the incident light. Hereby, the incident light can accurately couple into the wall 110a of the hollow tubular waveguide element 110 and undergoes multiple total internal reflections in the wall 110a of the hollow tubular waveguide element 110. Wherein, the number of the light emitting device 220 may be multiple and each of the light emitting devices 220 may respectively enter the wall 110a from different locations of the proximal end 111 of the wall 110a through the corresponding first optical fibers 241, so as to increase the entire light intensity of the incident light.

In addition, the reflection-based tubular waveguide particle plasmon resonance sensing system of the present invention can further comprise a second optical fiber 242 disposed between the photodetector 230 and the hollow tubular waveguide element 110. For example, one end point of the second optical fiber 242 is connected to the proximal end 111 of the wall 110a of the hollow tubular waveguide element 110, and the other end point is connected to the photodetector 230, such that the emergent light emitted from the proximal end 111 of the wall 110a can be accurately directed to the photodetector 230 by the second optical fiber 242 and the photodetector 230 receives the emergent light from the second optical fiber 242 completely. Wherein, the number of the second optical fiber 242 may be multiple, and the second optical fiber 242 and the first optical fiber 241 may be arranged at the proximal end 111 of the wall 110a of the hollow tubular waveguide element 110 in special arrangement. Wherein, the cross-sectional diagram of the projection of the end points of the first optical fibers 241 and the second optical fibers 242 on the proximal end 111 of the wall 110a can be shown as the region A1, but it shall be not limited thereto.

For example, the reflection-based tubular waveguide particle plasmon resonance sensing system of the present invention may follow the order of disposing one first optical fiber 241 and two second optical fibers 242 at the proximal end 111 of the wall 110a of the hollow tubular waveguide element 110, and the above order is repeated again with consideration of adequate space between the fibers. Wherein, when the number of first optical fiber 241 has a total of four, the number of second optical fiber 242 has a total of eight, but it shall be not limited thereto. That is to say, the number of the first optical fiber 241 may be 2, 4, 6, 8 or 10, and the number of the second optical fiber 242 corresponding to the first optical fiber 241 may be 10, 8, 6, 4, or 2. Wherein, the first optical fibers 241 and the second optical fibers 242 are arranged in specified order with adequate space in between, such that the first optical fibers 241 and the second optical fibers 242 can be distributed equally. Hereby, the photodetector 230 can receive the emergent light more completely.

When the photodetector 230 receives the emergent light, which is the light exited from the proximal end 111, the reflection-based tubular waveguide particle plasmon resonance sensing system of the present invention can measure the light intensity of the emergent light and thereby obtain the characteristics of the sample. For example, the reflection-based tubular waveguide particle plasmon resonance sensing system of the present invention can further comprise a printed circuit board 250, an analog to digital converter 260 and a processor 270. Wherein, the printed circuit board 250 is electrically connected between the analog to digital converter 260 and the photodetector 230, and transmits the light intensity signal received by the photodetector 230 to the analog to digital converter 260. Besides, the analog to digital converter 260 is also electrically connected to the function generator 210 to receive the signal generated by the function generator 210. That is, the analog to digital converter 260 obtains the signal of the incident light entering into the wall 110a of the hollow tubular waveguide element 110 from the function generator 210 and obtains the light intensity signal of the emergent light of the wall 110a detected by the photodetector 230 through the printed circuit board 250. Afterwards, the analog to digital converter 260 converts the signals of the incident light and the emergent light into the digital signals and transmits the digital signals to the processor 270 electrically connected to the analog to digital converter 260. The processor 270 accordingly calculates and analyzes the received digital signals to obtain the characteristics (e.g. refractive index, concentration, and so on) of the sample. In addition, the reflection-based tubular waveguide particle plasmon resonance sensing system of the present invention can further comprise a display device 280 electrically connected to the processor 270, such that the processor 270 transmits the processed result and/or the received digital signal (may become the analog signal after being processed) to the display device 280. Then, the display device 280 displays the processed result and/or the received signal (no matter the digital signal or the analog signal) processed by the processor 270. That is to say, the reflection-based tubular waveguide particle plasmon resonance sensing system of the present invention can enable the user to obtain the detected signal and/or the result instantly via the display device 280 by displaying the result and/or the signal. Wherein, the analog to digital converter 260 may be a common signal processing and data acquisition card, and the processor 270 may be a microcomputer.

Furthermore, in order to demonstrate the reflection-based tubular waveguide particle plasmon resonance sensing system and the sensing device thereof of the present invention indeed having the optimal sensing function, the applicant further employs a number of samples having different refractive indexes (e.g. aqueous sucrose solution having different refractive indexes) and having different concentrations of biomolecules to respectively examine the refractive index sensing function and biosensing function of the reflection-based tubular waveguide particle plasmon resonance sensing system and the sensing device thereof of the present invention.

Figure 4:
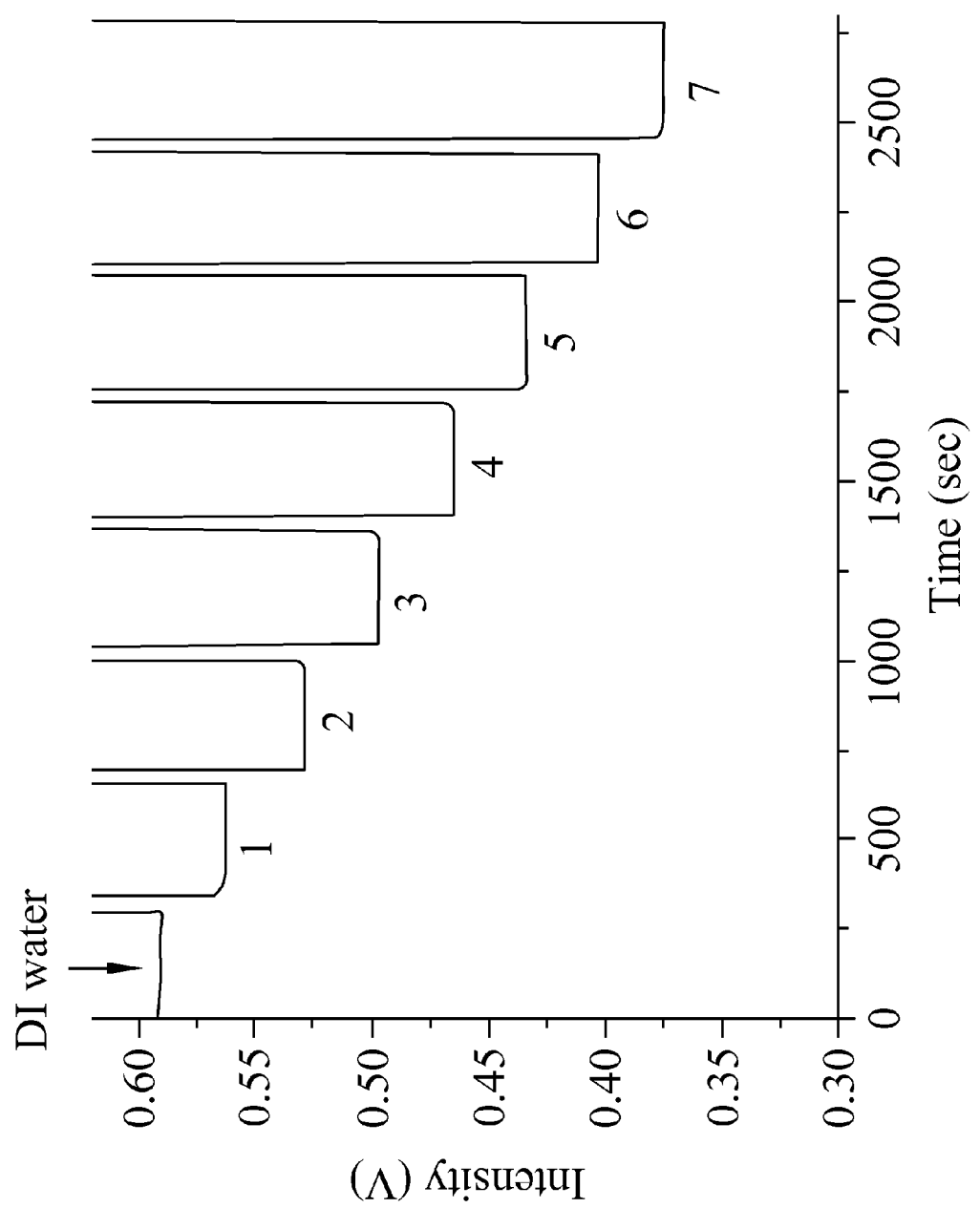
FIG. 4 is a real-time detection diagram showing the sensor responses in solutions of different refractive indexes measured by a reflection-based tubular waveguide particle plasmon resonance sensing system of the present invention.
Figure 5:
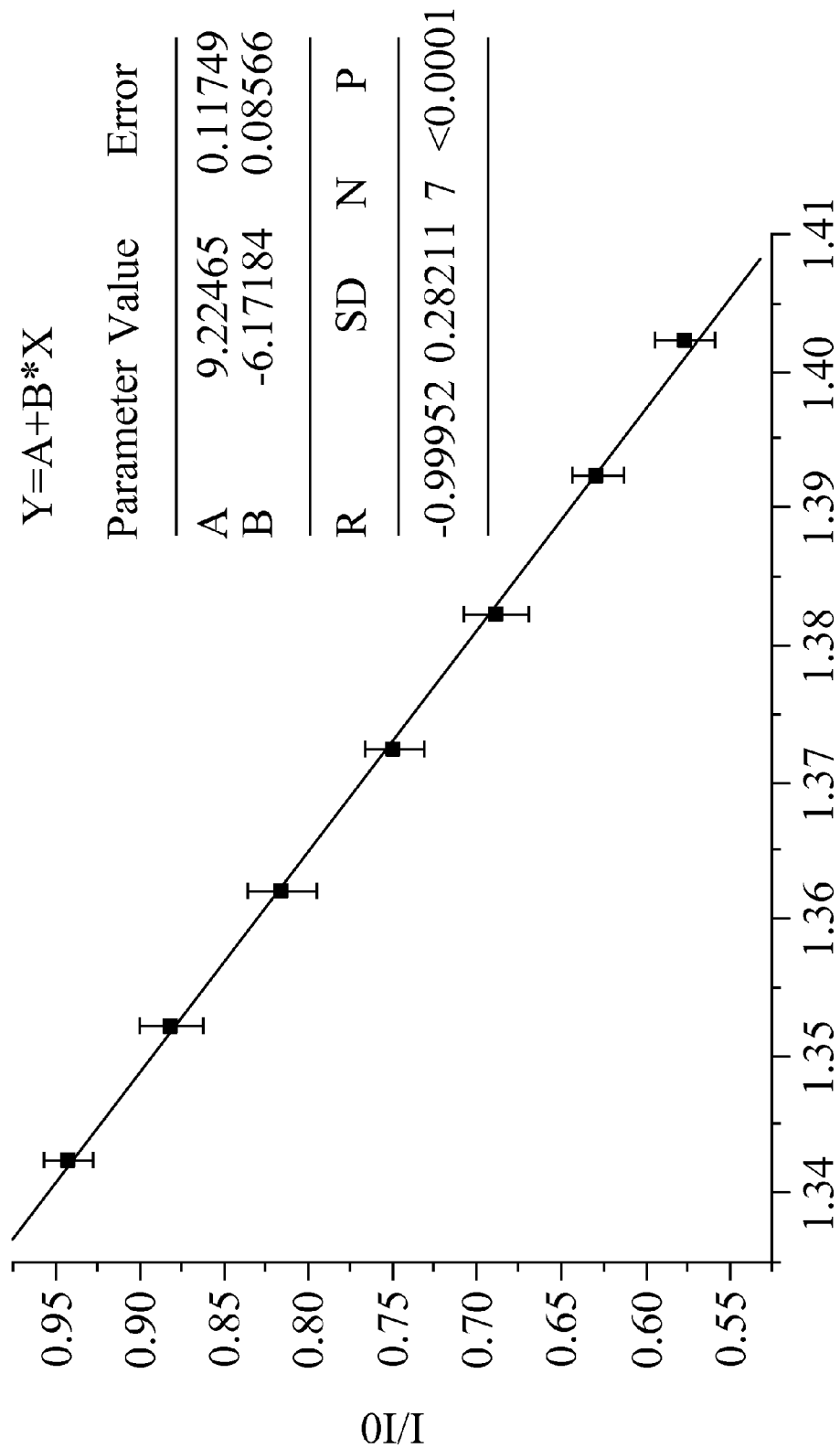
FIG. 5 is a calibration graph showing the sensor response versus the refractive index of the solutions measured by a reflection-based tubular waveguide particle plasmon resonance sensing system of the present invention.

Please refer to FIG. 4 and FIG. 5, which are a real-time detection diagram showing the sensor responses of a reflection-based tubular waveguide particle plasmon resonance sensing system of the present invention in solutions of different refractive indexes and a calibration graph showing the responses versus the refractive indexes of the solutions measured by the reflection-based tubular waveguide particle plasmon resonance sensing system of the present invention, respectively. Wherein, the sample numbers 1-7 of FIG. 4 respectively denote that the reflection-based tubular waveguide particle plasmon resonance sensing device 100 is placed into the samples (e.g. aqueous sucrose solution) having different refractive indexes. Wherein, the relation between the sample numbers and the refractive indexes of the samples is shown as Table 1.

TABLE 1

| | Solution No. | | | | | | |
|---|---|---|---|---|---|---|---|
| | 1 | 2 | 3 | 4 | 5 | 6 | 7 |
| Concentration of sucrose (wt %) | 6.8 | 13.3 | 19.5 | 25.4 | 31.1 | 36.6 | 41.7 |
| Refractive index | 1.343 | 1.353 | 1.363 | 1.373 | 1.383 | 1.393 | 1.403 |

In the detection, samples of deionized (DI) water and aqueous sucrose solutions having different refractive indexes (corresponding to the solution numbers 1-7) are separately injected into the sample containers, and then the reflection-based tubular waveguide particle plasmon resonance sensing device 100 is placed into the sample containers sequentially to perform the real-time detection with the samples of deionized (DI) water and solutions having different refractive indexes (the light intensity versus the time are as shown in FIG. 4). Wherein the processor 270 uses the signal of the deionized water sample (I0) detected by the reflection-based tubular waveguide particle plasmon resonance sensing device 100 as a reference to perform the normalization of the signal of other samples (I), then demonstrates the normalized signal (I/I0) of the solutions having different refractive indexes versus the refractive index to obtain the linear regression between the normalized signal and the refractive index (as shown in FIG. 5). As shown in FIG. 4 and FIG. 5, it can be found that the light intensity of the emergent light of the reflection-based tubular waveguide particle plasmon resonance sensing system and the sensing device thereof of the present invention decreases with the increase of the refractive index. The obtained refractive index sensitivity of the sensing device is $-6.17$ $RIU^{-1}$, the refractive index resolution of the sensing device is $2.21 \times 10^{-5}$ RIU. Hence, it demonstrates that the reflection-based tubular waveguide particle plasmon resonance sensing system and the sensing device thereof of the present invention can perform the real-time detection for liquid samples of different refractive indexes.

Figure 6:
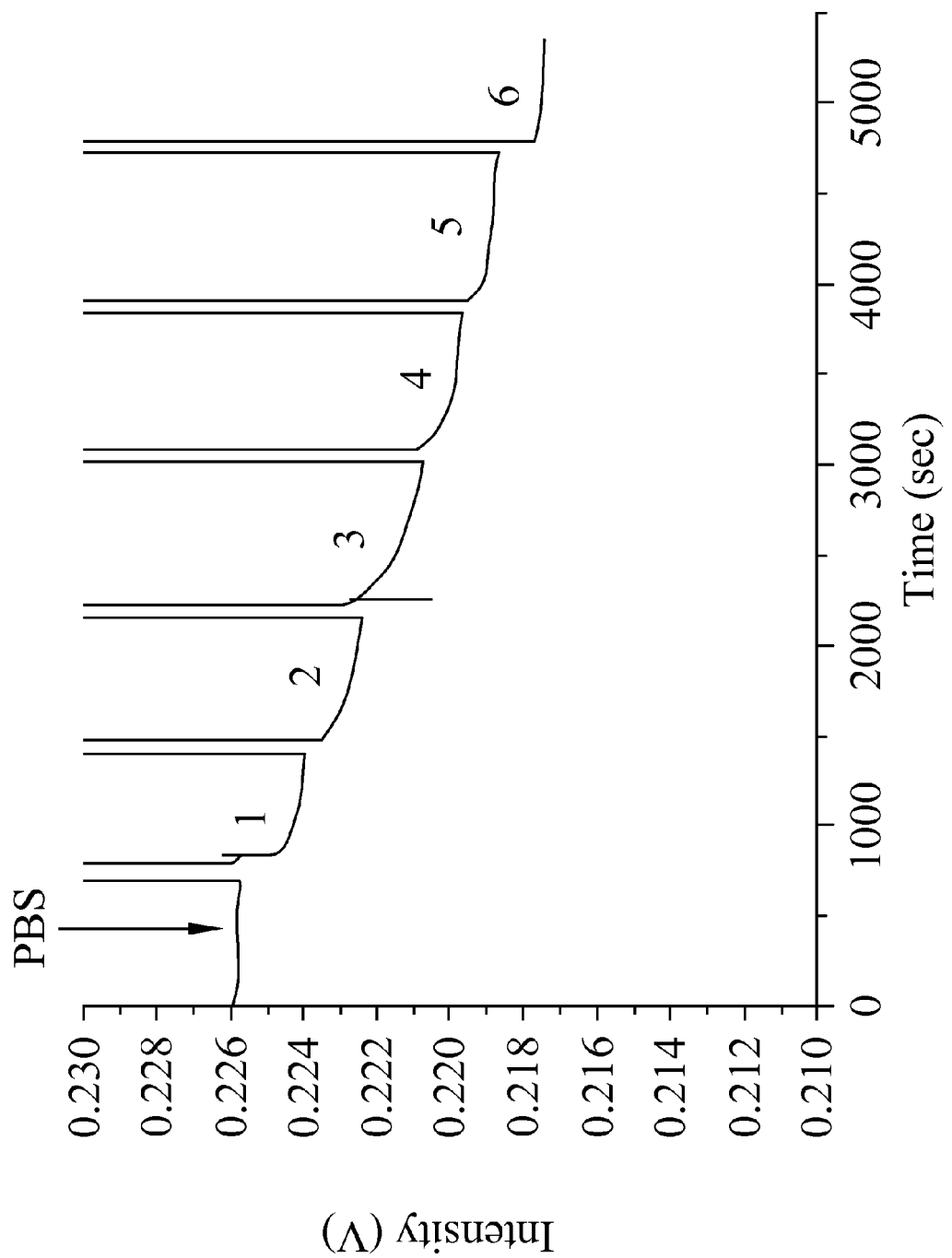
FIG. 6 is a real-time detection diagram showing the sensor responses in solutions of different concentrations of anti-OVA measured by a reflection-based tubular waveguide particle plasmon resonance sensing system of the present invention.
Figure 7:
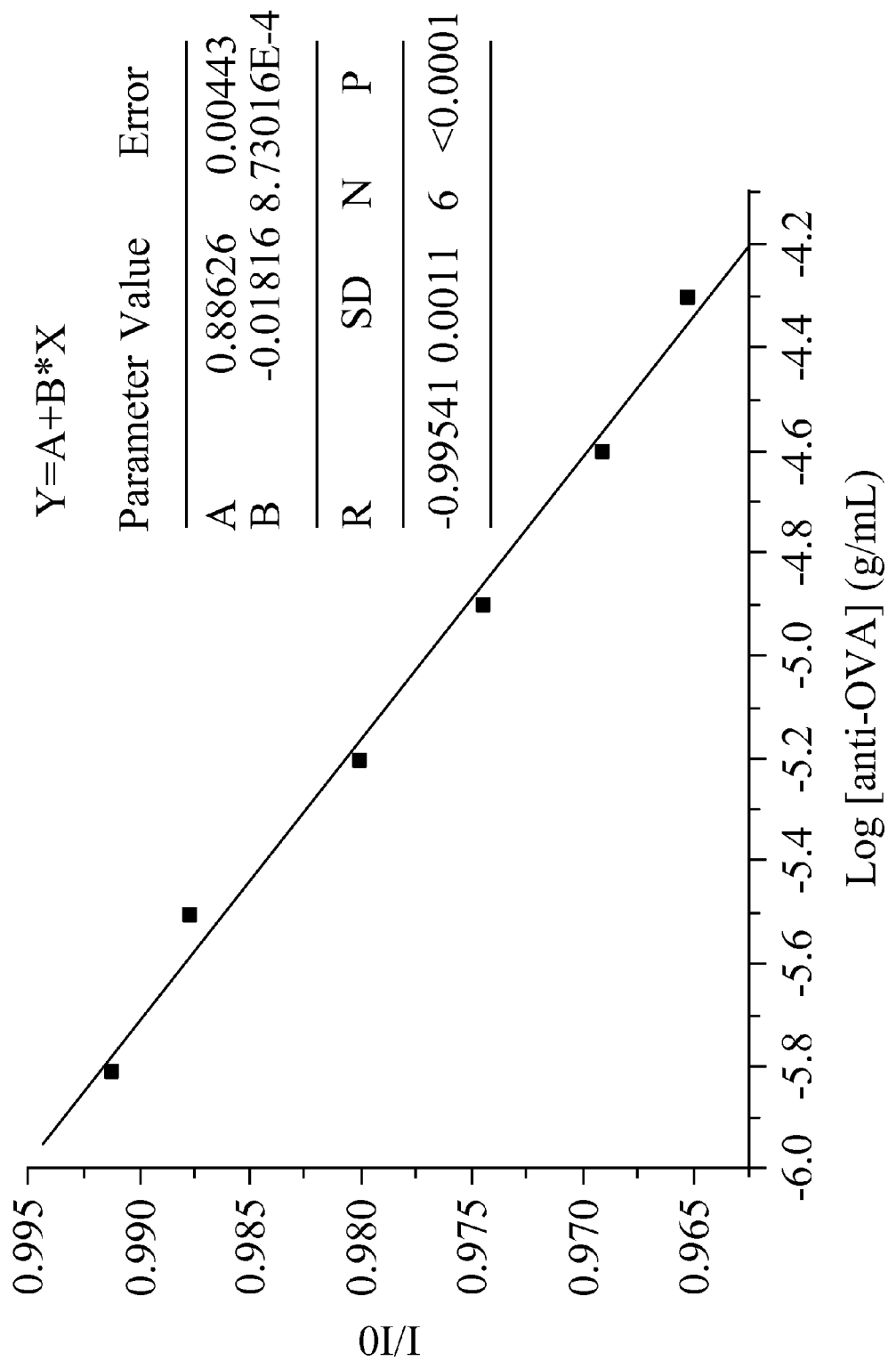
FIG. 7 is a calibration graph showing the sensor response versus the concentration of anti-OVA measured by a reflection-based tubular waveguide particle plasmon resonance sensing system of the present invention.

Besides, please refer to FIG. 6 and FIG. 7. FIG. 6 is a real-time detection diagram showing the sensor responses in samples of different concentrations of anti-OVA (ovalbumin) measured by a reflection-based tubular waveguide particle plasmon resonance sensing system with the recognition unit, ovalbumin (OVA), of the present invention. FIG. 7 is a calibration graph showing the sensor response versus concentration of anti-OVA measured by a reflection-based tubular waveguide particle plasmon resonance sensing system of the present invention. Wherein, the sample numbers 1-6 shown in FIG. 6 respectively denote that the reflection-based tubular waveguide particle plasmon resonance sensing device 100 is placed into the samples having different concentrations of anti-OVA. Wherein, the relation between the sample numbers and the samples having different concentrations of anti-OVA is shown as Table 2.

TABLE 2

| | Solution No. | | | | | |
|---|---|---|---|---|---|---|
| | 1 | 2 | 3 | 4 | 5 | 6 |
| Concentration of anti-OVA ($10^{-6}$ g/ml) | 1.56 | 3.13 | 6.25 | 12.5 | 25.0 | 50.0 |

In the detection, the recognition unit, such as OVA, is modified on the surface of the noble metal nanoparticle layer 130 for performing the detection. Wherein, the samples having different concentrations of anti-OVA are placed into different sample containers, and phosphate buffered saline (PBS) is served as the reference. Afterwards, the reflection-based tubular waveguide particle plasmon resonance sensing device 100 is sequentially placed into the sample containers to perform the real-time detection with different concentrations of anti-OVA. The diagram showing the light intensity versus the time is shown as FIG. 6. Wherein, under the reflection based tubular waveguide particle plasmon resonance sensing system of the present invention, the light intensity of the emergent light exited the proximal end 111 decreases according to a molecular binding kinetics curve. Besides, the processor 270 uses the light intensity of the emergent light detected at the condition of using the PBS as the reference to perform the normalization, then demonstrates the normalized signal (I/I0) of the samples having different anti-OVA concentrations versus the logarithmic anti-OVA concentration to obtain the linear regression between the normalized signal and the anti-OVA concentration (as shown in FIG. 7). As shown, the limit of detection (LOD) of detecting the anti-OVA concentration is about $5.71 \times 10^{-7}$ g/mL ($3.81 \times 10^{-9}$ M). The result indicates that the reflection-based tubular waveguide particle plasmon resonance sensing system and the sensing device thereof of the present invention are able to perform the biosensing measurements.

As a result, the reflection-based tubular waveguide particle plasmon resonance sensing system and the sensing device thereof of the present invention indeed have optimal sensing function.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. A reflection-based tubular waveguide particle plasmon resonance sensing device, comprising:
    a hollow tubular waveguide element having a wall, wherein two openings are disposed at a distal end and a proximal end opposed to each other of the hollow tubular waveguide element;
    a reflection layer disposed on the distal end of the wall of the hollow tubular waveguide element, wherein a light enters the wall through the proximal end and is total internal reflected many times along the wall, then the light is reflected by the reflection layer and is total internal reflected many times along the wall again, then the light exits the wall through the proximal end; and
    a noble metal nanoparticle layer having a plurality of noble metal nanoparticles that is distributed on both of internal and external side surfaces of the wall associated the hollow tubular waveguide element, wherein when a sample contacts the noble metal nanoparticle layer, a particle plasmon resonance condition of the noble metal nanoparticle layer is altered by the sample, and hence a signal intensity of the light exiting the proximal end of the hollow tubular waveguide element changes.

2. The reflection-based tubular waveguide particle plasmon resonance sensing device of claim 1, wherein the material of the hollow tubular waveguide element is a transparent material.

3. The reflection-based tubular waveguide particle plasmon resonance sensing device of claim 1, wherein the noble metal nanoparticle layer has a plurality of noble metal nanoballs, a plurality of noble metal nanorods, a plurality of noble metal nanoshells, a plurality of noble metal nanorings, a plurality of noble metal nanoplates, a plurality of noble metal nano dendrimer-like, a plurality of noble metal nanocubes, a plurality of noble metal nanoprisms, a plurality of noble metal nanonetworks, or the combination thereof.

4. The reflection-based tubular waveguide particle plasmon resonance sensing device of claim 1, wherein the noble metal nanoparticle layer is modified by a recognition unit for being applied to detecting different substances, wherein when the sample contacts the noble metal nanoparticle layer and an analyte in the sample binds with the recognition unit, the particle plasmon resonance condition is altered and hence the signal intensity of the light exiting the proximal end of the hollow tubular waveguide element changes; wherein the recognition unit includes at least on of a chemical recognition molecule, and antibody, an antigen, a lectin, a hormone receptor, a nucleic acid, and a carbohydrate.

5. The reflection-based tubular waveguide particle plasmon resonance sensing device of claim 1, wherein the material of the distal end of the hollow tubular waveguide element is a reflective material for being used as the reflection layer.

6. The reflection-based tubular waveguide particle plasmon resonance sensing device of claim 1, further comprising a refractive index adjustment layer disposed on part of the external side surface and/or the internal side surface with the noble metal nanoparticle layer for avoiding the light being disturbed by the sample outside the wall when the sample contacts the external side surface and the internal side surface, wherein the refractive index of the refractive index adjustment layer is lower than the refractive index of the hollow tubular waveguide element.

7. A reflection-based tubular waveguide particle plasmon resonance sensing system, comprising:
    at least one light emitting device for providing at least one light;
    a hollow tubular waveguide element having a wall, wherein two openings are disposed at a distal end and a proximal end opposed to each other of the hollow tubular waveguide element, wherein the light enters the wall through the proximal end and is total internal reflected many times along the wall;
    a reflection layer disposed on the distal end of the wall of the hollow tubular waveguide element and reflecting the light entered in the wall, such that the light is total internal reflected many times along the wall again and exits the wall through the proximal end;
    a noble metal nanoparticle layer having a plurality of noble metal nanoparticles that is distributed on both of internal and external side surfaces of the wall associated the hollow tubular waveguide element, wherein when a sample contacts the noble metal nanoparticle layer, a particle plasmon resonance condition of the noble metal nanoparticle layer is altered by the sample, and hence a signal intensity of the light exiting the proximal end of the hollow tubular waveguide element changes; and
    at least one photodetector disposed on the side of the proximal end of the hollow tubular waveguide element, wherein the photodetector detects the light exited the wall through the proximal end for determining the sample.

8. The reflection-based tubular waveguide particle plasmon resonance sensing system of claim 7, further comprising a moving device holding the light emitting device, the hollow tubular waveguide element, the reflection layer, the noble metal nanoparticle layer, and the photodetector, wherein the moving device is configured to move the light emitting device, the hollow tubular waveguide element, the reflection layer, the noble metal nanoparticle layer, and the photodetector.

9. The reflection-based tubular waveguide particle plasmon resonance sensing system of claim 7, further comprising a sample container holding the sample and being disposed on one side of the hollow tubular waveguide element.

10. The reflection-based tubular waveguide particle plasmon resonance sensing system of claim 7, further comprising a suction device disposed on one side of the hollow tubular waveguide element for drawing the sample into the hollow tubular waveguide element.

11. The reflection-based tubular waveguide particle plasmon resonance sensing system of claim 7, wherein the material of the hollow tubular waveguide element is a transparent material.

12. The reflection-based tubular waveguide particle plasmon resonance sensing system of claim 7, further comprising a refractive index adjustment layer disposed on part of the external side surface and/or the internal side surface with the noble metal nanoparticle layer for avoiding the light being disturbed by the sample outside the wall when the sample contacts the external side surface and the internal side surface, wherein the refractive index of the refractive index adjustment layer is lower than the refractive index of the hollow tubular waveguide element.

13. The reflection-based tubular waveguide particle plasmon resonance sensing system of claim 7, wherein the noble metal nanoparticle layer is modified by a recognition unit for being applied to detecting different substances, wherein when the sample contacts the noble metal nanoparticle layer and an analyte in the sample binds with the recognition unit, the particle plasmon resonance condition is altered and hence the signal intensity of the light exiting the proximal end of the hollow tubular waveguide element changes; wherein the recognition unit includes at least one of a chemical recognition molecule, and antibody, and antigen, a lectin, a hormone receptor, a nucleic acid, and a carbohydrate.

* * * * *